(12) United States Patent
Long et al.

(10) Patent No.: US 11,311,662 B2
(45) Date of Patent: *Apr. 26, 2022

(54) MULTI-CONDUIT MANIFOLDS, SYSTEMS, AND METHODS FOR APPLYING REDUCED PRESSURE TO A SUBCUTANEOUS TISSUE SITE

(71) Applicant: KCI Licensing, Inc., San Antonio, TX (US)

(72) Inventors: Justin Alexander Long, San Antonio, TX (US); Michael E. Manwaring, San Antonio, TX (US); Douglas A. Cornet, Charlottesville, VA (US)

(73) Assignee: KCI Licensing, Inc., San Antonio, TX (US)

( * ) Notice: Subject to any disclaimer, the term of this patent is extended or adjusted under 35 U.S.C. 154(b) by 546 days.

This patent is subject to a terminal disclaimer.

(21) Appl. No.: 16/352,630

(22) Filed: Mar. 13, 2019

(65) Prior Publication Data

US 2019/0216990 A1    Jul. 18, 2019

Related U.S. Application Data

(60) Continuation of application No. 14/489,173, filed on Sep. 17, 2014, now Pat. No. 10,258,722, which is a
(Continued)

(51) Int. Cl.
*A61M 1/00* (2006.01)
*A61M 25/00* (2006.01)

(52) U.S. Cl.
CPC ............ *A61M 1/85* (2021.05); *A61M 25/003* (2013.01); *A61M 2025/0034* (2013.01);
(Continued)

(58) Field of Classification Search
CPC ................................................ Y10T 29/49826
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Guy K Townsend

(57) ABSTRACT

The illustrative embodiments described herein are directed to systems, methods, and apparatuses for applying a reduced pressure to a subcutaneous tissue site. In one instance, a manifold for applying reduced pressure to a subcutaneous tissue site includes a plurality of first conduits, each of the plurality of first conduits having a wall with at least one first aperture and at least one second aperture. At least one of the plurality of first conduits is operable to deliver reduced pressure to the subcutaneous tissue site. The plurality of first conduits is coupled in a spaced arrangement that forms an interior space. The manifold further includes a second conduit comprising the interior space and formed by a portion of each wall of the plurality of first conduits. The second conduit is in fluid communication with the plurality of first conduits via the at least one second aperture.

6 Claims, 3 Drawing Sheets

Related U.S. Application Data division of application No. 12/641,546, filed on Dec. 18, 2009, now Pat. No. 8,864,728.

(60) Provisional application No. 61/141,728, filed on Dec. 31, 2008.

(52) U.S. Cl.
CPC . *A61M 2025/0036* (2013.01); *A61M 2205/04* (2013.01); *Y10T 29/49826* (2015.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A * | 7/1983 | Muto | A61M 25/0111 128/DIG. 26 |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,650,463 A * | 3/1987 | LeVeen | A61M 1/84 604/43 |
| 4,655,754 A | 4/1987 | Richmond et al. | |
| 4,664,662 A | 5/1987 | Webster | |
| 4,710,165 A | 12/1987 | McNeil et al. | |
| 4,717,379 A * | 1/1988 | Ekholmer | A61M 25/007 604/43 |
| 4,721,123 A * | 1/1988 | Cosentino | A61M 25/002 134/113 |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A * | 1/1990 | Poirier | A61L 29/041 128/DIG. 26 |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,116,310 A * | 5/1992 | Seder | A61M 27/00 604/266 |
| 5,134,994 A | 8/1992 | Say | |
| 5,149,331 A * | 9/1992 | Ferdman | A61M 1/90 604/290 |
| 5,167,613 A | 12/1992 | Karami et al. | |
| 5,176,663 A | 1/1993 | Svedman et al. | |
| 5,215,522 A | 6/1993 | Page et al. | |
| 5,232,453 A * | 8/1993 | Plass | A61M 25/02 128/DIG. 26 |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A * | 10/1994 | Svedman | A61M 27/00 604/313 |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,562,653 A * | 10/1996 | Thompson | A61L 29/06 424/428 |
| 5,569,165 A * | 10/1996 | Chin | A61B 17/0218 294/81.3 |
| 5,607,388 A | 3/1997 | Ewall | |
| 5,636,643 A | 6/1997 | Argenta et al. | |
| 5,645,081 A | 7/1997 | Argenta et al. | |
| 5,749,826 A * | 5/1998 | Faulkner | A61M 25/04 600/29 |
| 5,785,706 A * | 7/1998 | Bednarek | A61M 25/0662 600/372 |
| 5,919,188 A * | 7/1999 | Shearon | A61B 18/1492 606/41 |
| 6,010,500 A * | 1/2000 | Sherman | A61B 18/1492 606/41 |
| 6,071,267 A | 6/2000 | Zamierowski | |
| 6,080,151 A * | 6/2000 | Swartz | A61B 18/1492 606/45 |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 6,936,037 B2 * | 8/2005 | Bubb | A61M 1/90 604/327 |
| 7,235,070 B2 * | 6/2007 | Vanney | A61B 18/1492 606/41 |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |

(56) References Cited

U.S. PATENT DOCUMENTS

| | | | |
|---|---|---|---|
| 8,679,081 B2 | 3/2014 | Heagle et al. | |
| 8,834,451 B2 | 9/2014 | Blott et al. | |
| 8,864,728 B2* | 10/2014 | Long | A61M 25/003 604/319 |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 10,258,722 B2* | 4/2019 | Long | A61M 25/003 604/319 |
| 2002/0077661 A1* | 6/2002 | Saadat | A61F 2/30756 606/221 |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2005/0004534 A1* | 1/2005 | Lockwood | A61M 1/74 604/304 |
| 2005/0055019 A1* | 3/2005 | Skarda | A61B 18/1492 606/41 |
| 2006/0079852 A1* | 4/2006 | Bubb | A61M 1/74 604/317 |
| 2007/0005051 A1* | 1/2007 | Kampa | A61B 18/1492 606/41 |
| 2007/0060935 A1* | 3/2007 | Schwardt | A61B 17/3207 606/170 |
| 2007/0219471 A1* | 9/2007 | Johnson | A61B 17/88 601/6 |
| 2009/0306631 A1* | 12/2009 | Santora | A61M 25/003 604/543 |
| 2010/0168692 A1* | 7/2010 | Collins | A61M 1/90 604/319 |
| 2012/0203144 A1* | 8/2012 | Collins | A61M 1/90 601/6 |
| 2014/0163491 A1 | 6/2014 | Schuessler et al. | |
| 2015/0045726 A1* | 2/2015 | Long | A61M 1/85 604/28 |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds" Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems

(56) References Cited

OTHER PUBLICATIONS in Modern Clinical Surgery: Interdepartmental Collection, edited by V. Ye Volkov et al. (Chuvashia State University, Cheboksary, U.S.S.R. 1986); pp. 94-96.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

MULTI-CONDUIT MANIFOLDS, SYSTEMS, AND METHODS FOR APPLYING REDUCED PRESSURE TO A SUBCUTANEOUS TISSUE SITE

RELATED APPLICATIONS

This application is a continuation application of U.S. patent application Ser. No. 14/489,173, filed Sep. 17, 2014, which is a divisional application of U.S. patent application Ser. No. 12/641,546, filed Dec. 18, 2009, now issued U.S. Pat. No. 8,864,728, which claims the benefit, under 35 U.S.C. § 119(e), of the filing of U.S. Provisional Patent Application Ser. No. 61/141,728, entitled "Multi-conduit Manifolds, Systems, and Methods for Applying Reduced Pressure To a Subcutaneous Tissue Site," filed Dec. 31, 2008, which is incorporated herein by reference for all purposes.

BACKGROUND

The present invention relates generally to medical treatment systems, and more particularly, multi-conduit manifolds, systems, and methods for applying reduced pressure to a subcutaneous tissue site.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing, and increased formulation of granulation tissue. More recently, reduced pressure treatments have been utilized at subcutaneous tissue sites.

SUMMARY

To alleviate existing short comings with reduced-pressure treatment systems, the illustrative embodiments described herein are directed to systems, methods, and apparatuses for applying a reduced pressure to a subcutaneous tissue site. According to an illustrative, non-limiting embodiment, a system for applying reduced pressure to a subcutaneous tissue site that includes a reduced-pressure source for supplying reduced pressure, a fluid source for supplying a fluid, and a manifold adapted for placement at the subcutaneous tissue site. The manifold includes a plurality of first conduits, each of the plurality of first conduits having a wall formed with at least one first aperture and at least one second aperture. At least one of the plurality of first conduits is in fluid communication with the reduced-pressure source and is operable to deliver the reduced pressure to the subcutaneous tissue site via the at least one first aperture. The manifold further includes a second conduit formed by a portion of each wall of the plurality of first conduits. The second conduit is in fluid communication with the plurality of first conduits via the at least one second aperture. The system may further include a delivery conduit fluidly coupled to the manifold and reduced-pressure source.

According to another illustrative, non-limiting embodiment, a manifold for applying reduced pressure to a subcutaneous tissue site includes a plurality of first conduits, each of the plurality of first conduits having a wall with at least one first aperture and at least one second aperture. At least one of the plurality of first conduits is operable to deliver reduced pressure to the subcutaneous tissue site via the at least one first aperture. The plurality of first conduits is coupled in a spaced arrangement that forms an interior space. The manifold further includes a second conduit comprising the interior space and formed by a portion of each wall of the plurality of first conduits. The second conduit is in fluid communication with the plurality of first conduits via the at least one second aperture.

According to another illustrative, non-limiting embodiment, a method for applying reduced pressure to a subcutaneous tissue site includes providing a manifold, applying the manifold to the subcutaneous tissue site, and supplying the reduced pressure to the manifold via a delivery conduit. The manifold includes a plurality of first conduits. Each of the plurality of first conduits has a wall with at least one first aperture and at least one second aperture. At least one of the plurality of first conduits is operable to deliver reduced pressure to the subcutaneous tissue site via the at least one first aperture. The plurality of first conduits are coupled in a spaced arrangement that forms an interior space. The manifold further includes a second conduit comprising the interior space and formed by a portion of each wall of the plurality of first conduits. The second conduit is in fluid communication with the plurality of first conduits via the at least one second aperture.

According to another illustrative, non-limiting embodiment, a method of manufacturing an apparatus that is applying reduced pressure to a subcutaneous tissue includes providing a plurality of first conduits. Each of the plurality of first conduits has a wall formed with at least one first aperture and at least one second aperture. At least one of the plurality of first conduits is operable to deliver reduced pressure to the subcutaneous tissue site via the at least one first aperture. The method further includes coupling the plurality of first conduits to one another to form a second conduit. The second conduit is formed by a portion of each wall of the plurality of first conduits and is in fluid communication with the plurality of first conduits via the at least one second aperture.

According to another illustrative, non-limiting embodiment, a medical manifold for delivering one or more fluids to a tissue site includes a plurality of exterior conduits coupled in a spaced relationships to define an interior space between the plurality of exterior conduits. The interior space comprises a central conduit. The medical manifold further includes a plurality of apertures formed on the plurality of external conduits.

According to another illustrative, non-limiting embodiment, a method of manufacturing a medical manifold includes forming four first conduits with each first conduit touching two other first conduits, forming a second conduit from the four first conduits, and using a core pin to create apertures in the first conduits and the second conduit.

Other features and advantages of the illustrative embodiments will become apparent with reference to the drawings and detailed description that follow.

BRIEF DESCRIPTION OF THE DRAWINGS

To provide a more complete understanding of the illustrative, non-limiting embodiments and certain of its features and advantages, reference is now made to the following description taken in conjunction with the accompanying drawings, in which.

DETAILED DESCRIPTION OF THE ILLUSTRATIVE EMBODIMENTS

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
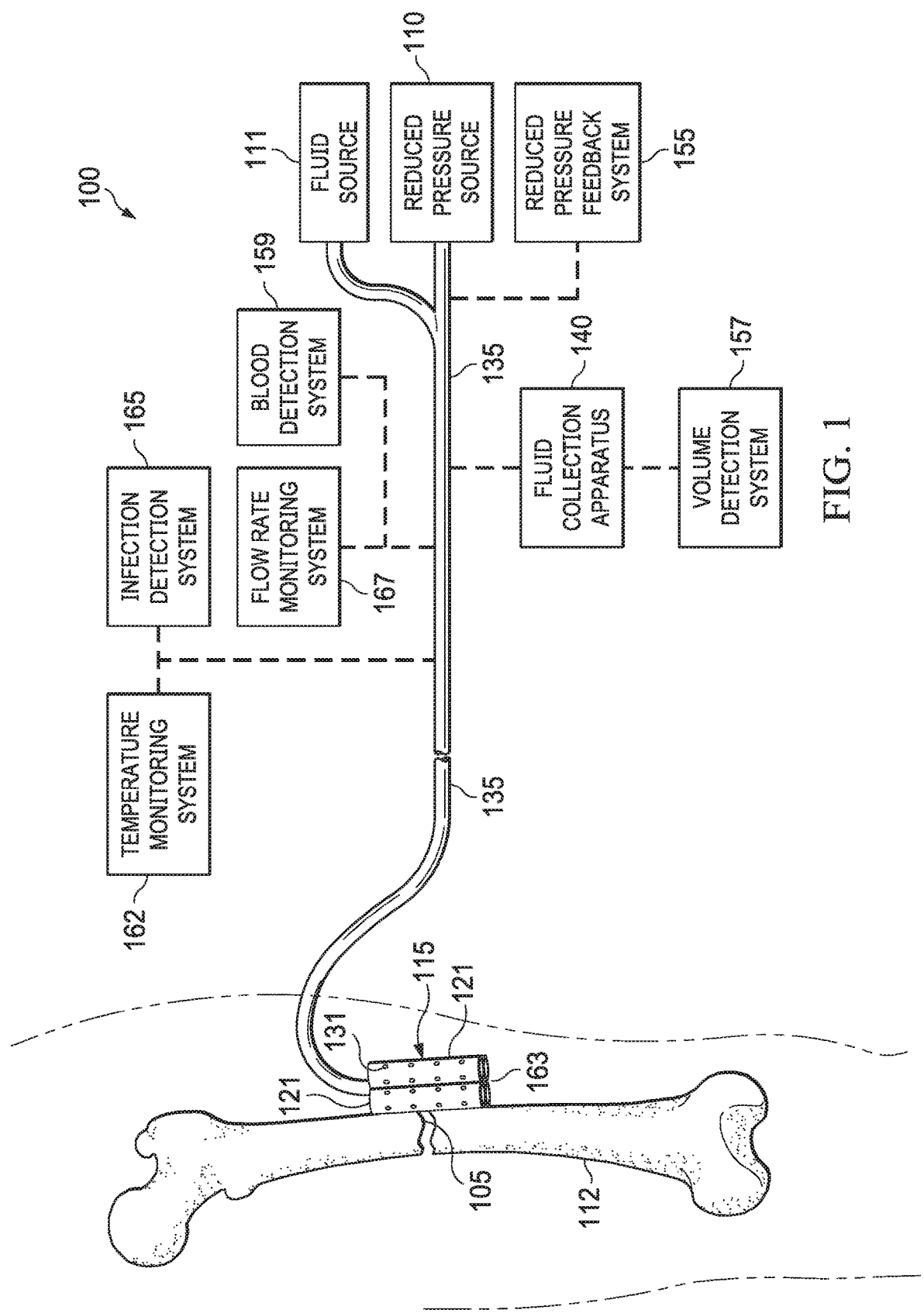
FIG. 1 is a schematic diagram of a reduced-pressure treatment system for applying reduced pressure to a subcutaneous tissue site in accordance with an illustrative embodiment.

Referring primarily to FIG. 1, a reduced-pressure treatment system 100, which applies reduced pressure to a tissue site 105, is shown according to an illustrative embodiment. In the non-limiting illustrative embodiment of FIG. 1, the tissue site 105 is a bone tissue site and, in particular, the tissue site 105 is a fracture on bone 112, which is a femur. It is believed that reduced pressure may provide a number of benefits. When used to promote bone tissue growth, reduced-pressure treatment may increase the rate of healing associated with a fracture, a non-union, a void, or other bone defects. Unless otherwise indicated, as used herein, "or" does not require mutual exclusivity. Reduced-pressure treatment may also be used to improve recovery from osteomyelitis. The treatment may further be used to increase localized bone densities in patients suffering from osteoporosis. Finally, reduced-pressure treatment may be used to speed and improve osseointegration of orthopedic implants, such as hip implants, knee implants, and fixation devices.

The tissue site 105 may also be the bodily tissue of any human, animal, or other organism, including adipose tissue, muscle tissue, dermal tissue, vascular tissue, connective tissue, cartilage, tendons, ligaments, or any other tissue. While the tissue site 105 may include a wound, diseased tissue, or defective tissue, the tissue site may also be healthy tissue that is not wounded, diseased, or defective. The application of reduced pressure to the tissue site 105 may be used to promote the drainage of exudate and other liquids from the tissue site 105, as well as stimulate the growth of additional tissue. In the case in which the tissue site 105 is a wound site, the growth of granulation tissue and removal of exudates and bacteria promote healing of the wound. The application of reduced pressure to non-wounded or non-defective tissue, including healthy tissue, may be used to promote the growth of tissue that may be harvested and transplanted to another tissue location.

The reduced pressure that is applied to the tissue site 105 is provided by a reduced-pressure source 110. As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site 105. Unless otherwise indicated, values of pressure stated herein are gauge pressures.

The reduced pressure delivered may be constant or varied (patterned or random) and may be delivered continuously or intermittently. Although the terms "vacuum" and "negative pressure" may be used to describe the pressure applied to the tissue site 105, the actual pressure applied to the tissue site 105 may be more than the pressure normally associated with a complete vacuum. Consistent with the use herein, an increase in reduced pressure or vacuum pressure typically refers to a relative reduction in absolute pressure.

The reduced-pressure source 110 may be any device or system that generates or provides a reduced pressure, including, but not limited to, manually operated or powered pumps. The possible sources of reduced pressure are numerous, and non-limiting examples follow. The reduced-pressure source 110 may include devices that are manually actuated, such as bellows pumps, peristaltic pumps, diaphragm pumps, rotary vane pumps, linear piston pumps, pneumatic pumps, hydraulic pumps, hand pumps, foot pumps, multi-chamber pumps, and manual pumps. As another non-limiting example, the reduced-pressure source 110 may be wall suction.

The reduced-pressure source 110 provides reduced pressure to tissue site 105 via a manifold 115, which may be percutaneously inserted and placed adjacent, or abutting, the tissue site 105. In one embodiment, the manifold 115 includes first conduits 121. Each of the first conduits 121 may have a plurality of or at least one first aperture 131. At least one of the first conduits 121 may be in fluid communication with the reduced-pressure source 110. In another embodiment, each of the first conduits 121 is in fluid communication with the reduced-pressure source 110. Also, at least one of the first conduits 121 may be operable to deliver reduced pressure to the tissue site 105 via the first apertures 131. In another embodiment, each of the first conduits 121 is operable to deliver reduced pressure to the tissue site 105 via the first apertures 131.

The manifold 115 may also include a second conduit 163 that is formed by a portion of each outer surface of the first conduits 121. The second conduit 163 may be in fluid communication with the first conduits 121 via at least one second aperture (see by analogy 240 in FIG. 2).

The reduced pressure provided by the reduced-pressure source 110 is provided to the manifold 115 via a reduced-pressure delivery conduit, delivery conduit 135. The delivery conduit 135 may deliver reduced pressure from the reduced-pressure source 110 to at least one of the first conduits 121 during treatment. In an alternative embodiment, the delivery conduit 135 may deliver reduced pressure to the second conduit 163.

The delivery conduit 135 may be coupled to the manifold 115. As used throughout, the term "coupled" includes coupling via a separate object. For example, the delivery conduit 135 is coupled to the manifold 115 if both the delivery conduit 135 and the manifold 115 are coupled to one or more third objects. The term "coupled" also includes "directly coupled," in which case the two objects touch each other in some way. The term "coupled" also encompasses two or more components that are continuous with one another by virtue of each of the components being formed from the same piece of material. The term "coupled" includes chemical coupling, such as via a chemical bond. The term "coupled" also includes fluidly coupled, in which case a first object that is coupled to a second object is in fluid communication with that second object. The term "coupled" may also include mechanical, thermal, or electrical coupling. Objects that are "coupled" may also be fixedly or removably coupled. The delivery conduit 135 is fluidly coupled to the manifold 115.

The delivery conduit 135 may be any tube or conduit through which a gas, liquid, gel, or other fluid may flow. The delivery conduit 135 may be made from any material, may be either flexible or inflexible, and may have any cross-sectional shape. The possible embodiments of the delivery conduit 135 are numerous, and non-limiting examples follow.

The delivery conduit 135 may include one or more paths or lumens through which fluid may flow. For example, the delivery conduit 135 may include two or more lumens. In this example, one or more lumens may be used to delivery reduced pressure from the reduced-pressure source 110 to at least one or all of the first conduits 121. Another lumen may be used to deliver fluids, such as air, liquid, antibacterial agents, antiviral agents, cell-growth promotion agents, irrigation fluids, or other chemically active agents from a fluid source 111, to the second conduit 163 of the manifold 115. These fluids may be used to purge (which includes partial purging) the manifold 115, including the purging of any blockages in the manifold 115.

Numerous other devices may be associated with The reduced-pressure treatment system 100 and typically with the delivery conduit 135. Non-limiting examples of devices include a reduced-pressure feedback system 155, a volume detection system 157, a fluid collection apparatus 140, a flow rate monitoring system 167, a blood detection system 159, an infection detection system 165, a temperature monitoring system 162, etc.

The reduced-pressure feedback system 155 may be operably associated with the other components of the reduced-pressure treatment system 100 to provide information to a user of the reduced-pressure treatment system 100 indicating a relative or absolute amount of pressure that is being delivered to the tissue site 105 or that is being generated by the reduced-pressure source 110. Examples of feedback systems include, without limitation, pop valves that activate when the reduced pressure rises above a selected value and deflection pop valves.

The volume detection system 157 may be included to detect the amount of fluid present in a fluid collection apparatus 140. The blood detection system 159 may be included to detect the presence of blood in exudate drawn from the tissue site 105. The temperature monitoring system 162 may be included to monitor the temperature of the tissue site 105. The infection detection system 165 may be included to detect the presence of infection at the tissue site 105. The infection detection system 165 may include a foam or other substance that changes color in the presence of bacteria. The foam or other substance may be operably associated with the delivery conduit 135 such that the color changing material is exposed to exudate from the tissue site 105. The flow rate monitoring system 167 may be included to monitor the flow rate of fluids drawn from the tissue site 105.

In addition to the above-mentioned components and systems, the reduced-pressure treatment system 100 may include valves, regulators, switches, and other electrical, mechanical, and fluid components to facilitate administration of reduced-pressure treatment to the tissue site 105. Other systems or devices may also be associated with the delivery conduit 135.

Figure 2:
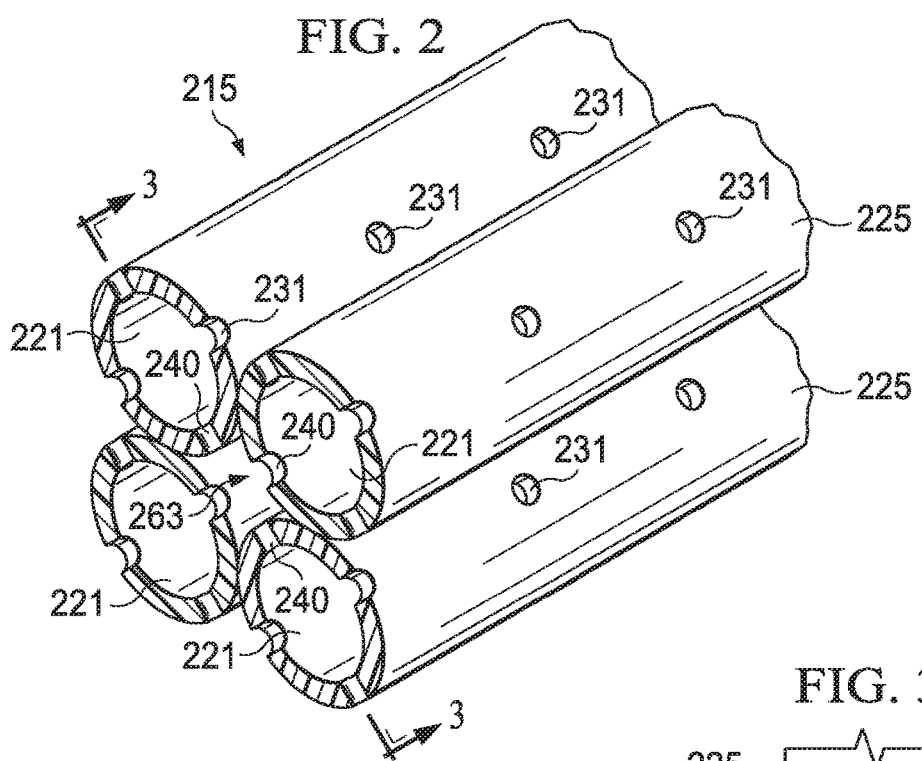
FIG. 2 is schematic, perspective view of a manifold according to an illustrative embodiment.
Figure 3:
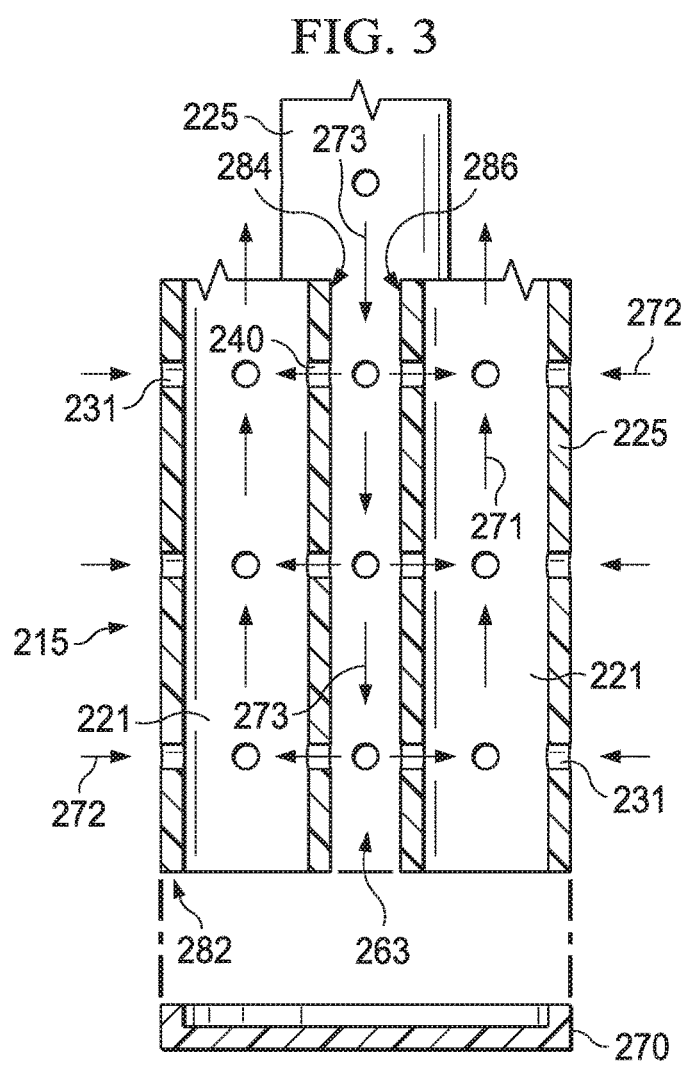
FIG. 3 is a schematic, longitudinal cross-sectional view of the manifold of FIG. 2.

Referring now primarily to FIGS. 2 and 3, a manifold 215 is shown according to an illustrative embodiment. The manifold 215 is a non-limiting example of the manifold 115 in FIG. 1. FIG. 3 is a longitudinal cross-sectional view of the manifold 215. The manifold 215 is adapted to be inserted into a patient and placed at the subcutaneous tissue site, e.g., tissue site 105 in FIG. 1. The manifold 215 includes a plurality of first conduits 221 that are adjacent to one another to form an interior space that defines a second conduit 263 between the first conduits 221. The plurality of first conduits 221 may be spaced in a uniform pattern or an irregular pattern and the members of the first plurality of conduits 221 may be uniform in size or vary. The first conduits 215 may be coupled one to another by a plurality of bonds, e.g., welds, cement, bonds, etc. The manifold 215 provides a reduced-pressure supply function and purging function using the first conduits 221 and second conduit 263. In one non-limiting example, the second conduit 263 may communicate with each of the first conduits 221 via a plurality of second apertures 240.

The manifold 215 includes first conduits 221. Each of the first conduits 221 has at least one first aperture 231 and at least one second aperture 240 formed in a wall 225, e.g., an annular wall. In the non-limiting examples of FIGS. 2 and 3, each of the first conduits 221 has a plurality of first apertures 231 and a plurality of second apertures 240 formed in the wall 225. The first apertures 231 may be uniformly or non-uniformly spaced from one another and may be uniform or non-uniform in diameter. Also, the second apertures 240 may be uniformly or non-uniformly spaced from one another and may be uniform or non-uniform in diameter.

In one illustrative embodiment, at least one of the first conduits 221 is in fluid communication with a reduced-pressure source, such as the reduced-pressure source 110 in FIG. 1. At least one of the first conduits 221 may deliver reduced pressure from the reduced-pressure source to a tissue site via the first apertures 231. The first conduits 221 may also deliver reduced pressure to any portion of the manifold 215, such as a distal end 282 of the manifold 215. In another illustrative embodiment, each of the first conduits 221 is in fluid communication with a reduced-pressure source, and each of first conduits 221 delivers reduced pressure to a subcutaneous tissue site via the first apertures 231. The flow of fluid in a direction away from the distal end 282 of the manifold 215 through the first conduits 221 is represented by the arrows 271. The flow of fluid away from the manifold 215 in this manner causes a reduced pressure at the first conduits 221 or at least a portion of the first conduits to be transferred to a tissue site via the first apertures 231.

Each the first apertures 231 allow fluid communication between the first conduits 221 and a space outside of the manifold 215, such as a tissue site. In addition to permitting the transfer of reduced pressure from the first conduits 221 to a tissue site, the first apertures 231 may also allow exudate or other fluid from the tissue site to enter the first conduits 221. The flow of fluid from the space outside of the manifold 215 into the first conduits 221 is represented by arrows 272.

The first conduits 221 are shown with a circular cross-sectional shape. However, the first conduits 221 may have any cross-sectional shape, including an elliptical, diamond, triangular, square, polygonal, etc.

In addition, although FIG. 2 shows the manifold 215 having four first conduits 221, the manifold 215 may have any number of first conduits. For example, the manifold 215 may have two or more first conduits 221 that at least partially encompass and form the second conduit 263. The second conduit 263 may be centrally disposed between the two or more first conduits 221 and typically between at least three of the first conduits 221.

Each of the first apertures 231 is shown to have a circular cross-sectional shape. However, each of the first apertures 231 may have any cross-sectional shape, such as an elliptical or polygonal cross-sectional shape. In another example, each of the first apertures 231 may be slits that extend along all or a portion of the first conduits 221. As used herein, a "slit" is any elongated hole, aperture, or channel. In one illustrative embodiment, each of the slits may be substantially parallel to one another.

The second conduit 263 of the manifold 215 is formed by a portion of each of the outer surfaces 284 and 286 of the first conduits 221. Each of the second apertures 240 is located on the portion of each of the outer surfaces 284 and 286 of the first conduits 221 that form the second conduit 263. The second conduit 263 is typically centrally formed, or otherwise disposed, between the first conduits 221. The second conduit 263, which is another non-limiting embodiment of the second conduit 163 in FIG. 1, is in fluid communication with the first conduits 221 via the second apertures 240.

The second conduit 263 may be in fluid communication with a fluid source, such as the fluid source 111, in FIG. 1 that supplies a fluid to the tissue site or portions of the first conduit 221. The second conduit 263 may receive fluid from the fluid source. In one embodiment, the second conduit 263 delivers the fluid to each of the first conduits 221 via the second apertures 240. The second conduit 263 may also deliver a fluid to a distal portion of the manifold 215, including the end of the manifold 215. The second conduit 263 may also deliver a fluid to the tissue space around the manifold 215. The fluid delivered by the second conduit 263 may be a gas, such as air, or a liquid. The flow of fluid delivered by the second conduit 263 is represented by arrows 273. In an alternative embodiment, fluid from a fluid source may be delivered toward the distal end 282 of the manifold 215 by any one or more of the first conduits 221.

In one non-limiting embodiment, the first conduits 221 draw fluid from the second conduit 263 via the second apertures 240. In this embodiment, reduced pressure from a reduced-pressure source causes the fluid to be drawn from the second conduit 263 to the first conduits 221 via the second apertures 240. In another non-limiting embodiment, positive pressure provided by the fluid source and delivered by the second conduit 263 forces, or otherwise causes, the fluid to be transferred from the second conduit 263 to the first conduits 221 via the second apertures 240. The transfer of fluid from the second conduit 263 to the first conduits 221 via the second apertures 240 facilitates the purging function of the manifold 215 that helps to remove or reduce any blockages that form in the manifold 215. The first conduits 221 may include any number of second apertures 240, which number may control the rate of fluid being transferred from the second conduit 263 to the first conduits 221.

In one embodiment, the manifold 215 may also include an end cap 270 that is adapted to be coupled or is coupled to the distal end 282 of the manifold 215 to form a distribution space. Fluid delivered by the second conduit 263 may be transferred from the second conduit 263 to the first conduits 221 via the space that is formed by coupling the end cap 270 to the distal end 282 of the manifold 215. In one embodiment, the space may provide the sole passageway through which fluid is transferred from the second conduit 263 to the first conduits 221. In this embodiment, no second apertures 240 may be present on the first conduits 221 or a minimal number of apertures 240.

In one illustrative embodiment, the second apertures 240 are absent or not open to the outside of the manifold 215 and fluid, such as liquid or air, may be drawn into the second conduit 263 by opening a valve to atmosphere (e.g., air purge). The valve is in fluid communication with the second conduit 263. Thus, fluid may be drawn through the second conduit 263 and back toward a reduced-pressure device via the first conduits 221, which, while under reduced pressure, may supply the force to draw any clot/clog formations, such as fibrin formations, out of the manifold 215 and toward the reduced-pressure source. In this embodiment, no supply port for the second conduit 263 may be present on the outer surface of the manifold 215. In this illustrative embodiment, the second conduit 263 may be completely enclosed by the first conduits 221, including a distal end of the second conduit 263, and thus may be closed from an outside environment, such as a tissue space. The second conduit 263 communicates proximate end cap 270 from the second conduit 263 to the first conduits 221. This illustrative embodiment may allow for a fluid to be contained within the manifold 215 as the fluid moves from the second conduit 263 to the first conduits 221. Thus, in this embodiment, the likelihood of the fluid moving out into the tissue space is reduced or eliminated.

In one illustrative, non-limiting embodiment, the manifold 215 is formed with four of the first conduits 221. As before, the first conduits 221 form the second conduit 263. Each of the four first conduits 221 touch at least two other of the four first conduits 221. In this embodiment, the four first conduits 221 and second conduit 263 are formed by co-extruding the conduits 221, 263. After the extruding the conduits 221, 263, a core pin may be used to pierce the conduits straight through to form the first apertures 231. Thus, for example, a core pin may pierce the upper right (for the orientation in FIG. 2) first conduit 221 and the lower left first conduit 221—and concomitantly pierce the second conduit 263. This may be repeated as many times as desired and at various orientations.

In the example in which the fluid in second conduit 263 is a liquid, the liquid may be pumped in or gravity fed down the second conduit 263 such that the only pathway for the liquid is through the second apertures 240 and into the first conduits 221, along the first conduits 221, and toward the reduced-pressure source. The manifold 215 preferably has a symmetrical design, and the symmetrical design of the manifold 215 allows the manifold 215 to be used in any spatial orientation to achieve the same or similar results in each position.

In another illustrative embodiment, a supplied fluid may be allowed to enter the space surrounding the manifold 215, such as a tissue space. For example, the fluid may exit the manifold 215 at the opening at the distal end 282 of the second conduit 263. The fluid may then be drawn into the first conduits 221.

In one illustrative embodiment, a method for applying reduced pressure to a subcutaneous tissue site includes applying the manifold 215 to the subcutaneous tissue site. The manifold 215 may be percutaneously inserted into a patient, and the manifold 215 may be positioned adjacent to or abutting the subcutaneous tissue site. The symmetrical design of the manifold 215 may facilitate the implantation of the manifold in any orientation.

In one illustrative embodiment, a method of manufacturing an apparatus for applying reduced pressure to a subcutaneous tissue site includes providing first conduits 221. The method may also include coupling the first conduits 221 to one another to form the second conduit 263. The second conduit 263 is formed by a portion of each outer surface 284 and 286 of the first conduits 221. The method may also include providing a delivery conduit for delivering reduced pressure to at least one of the first conduits 221. The method may also include fluidly coupling the delivery conduit to the first conduits 221 and the second conduit 263.

Figure 4:
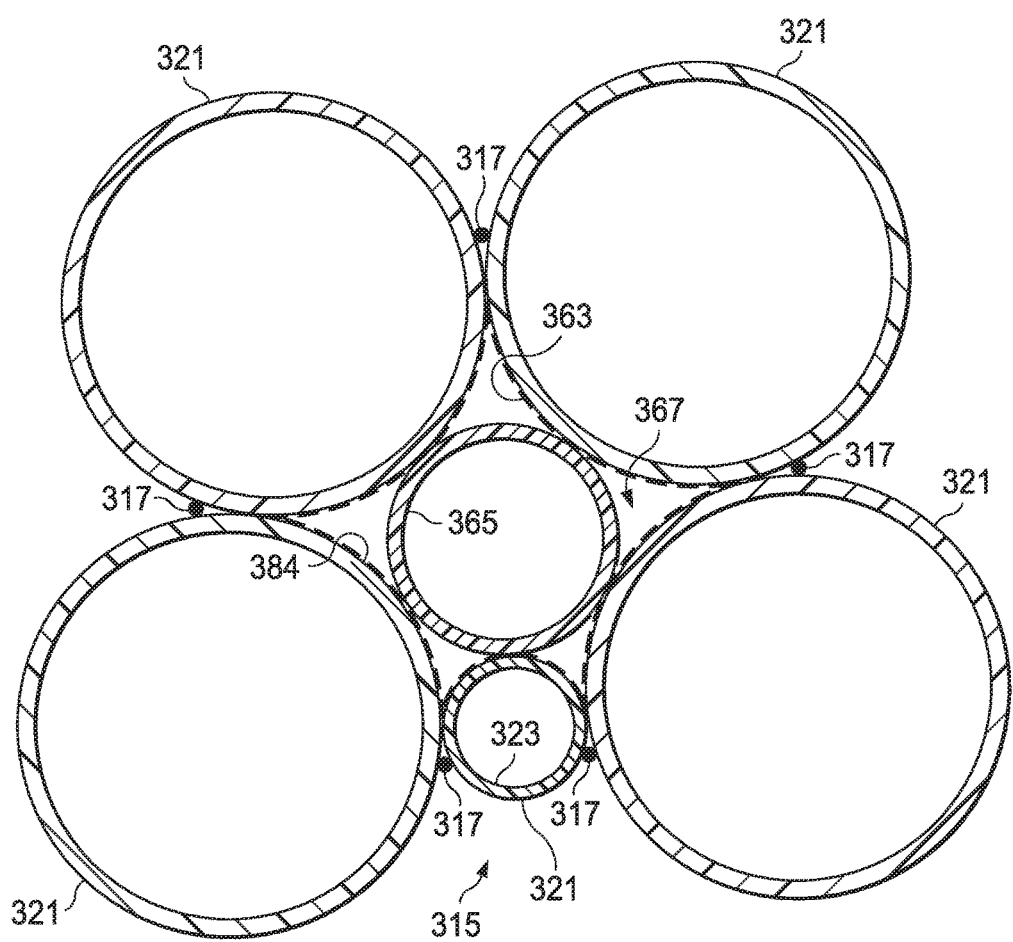
FIG. 4 is a schematic, lateral cross-sectional view of a manifold according to another illustrative embodiment.

Referring now primarily to FIG. 4, another illustrative, non-limiting embodiment of a manifold 315 is presented. The manifold 315 includes a plurality of first conduits 321 that are coupled in a spaced relationship with a plurality of bonds 317. Each of the plurality of first conduits 321 may have differing diameters or the same diameters, and in this illustrative embodiment, one conduit 323 of the first conduits conduit 321 is shown with a smaller diameter than the others. It should be understood in this and the other illustrative embodiments that the diameter of the first conduits may be varied or may be uniform.

The manifold 315 includes a second conduit 363 formed by a portion of each of the outer surfaces 384 of the first conduits 221. The second conduit 363 is shown with broken lines and in this illustration is a star-like shape. One or more additional conduits, such as third conduit 365, may be disposed within the second conduit 363. The additional conduit 365 may be sized to touch each of the plurality of first conduits 321 as shown or may be smaller in size. The additional conduit, or third conduit 365, may be coupled to one or more of the first conduits 221. In an alternative embodiment (not shown), the first conduits 321 may not form or fully form the second conduit, but the manifold 315 may have the additional conduit 365 at a center position adjacent to each of the first conduits 321.

The additional conduit 365 may carry a purging fluid or may be used to carry other fluids to or from a distal end (not shown) of the manifold 315. The space 367 formed exterior to the additional conduit 365 and on the interior of the second conduit 363 may carry a purging fluid to be introduced through apertures in the outer wall portion 384 of the first conduits 321, and the additional conduit 365 may carry a purging fluid to an end cap (e.g. end cap 270 in FIG. 3) to introduce a purging fluid into the first conduits 321 at the distal end. The end cap 270 may be attached to the distal end 282 using interference fit, RF welding, RF formed tip process, solvent bonding, or any other coupling technique.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A manifold for applying reduced pressure to a subcutaneous tissue site, the manifold comprising:
    a plurality of first conduits, each of the plurality of first conduits having a wall with at least one first aperture and at least one second aperture, at least one of the plurality of first conduits operable to deliver reduced pressure to the subcutaneous tissue site via the at least one first aperture;
    wherein the plurality of first conduits are coupled in a spaced arrangement that forms an interior space;
    a second conduit comprising the interior space and formed by a portion of each wall of the plurality of first conduits, the second conduit being in fluid communication with the plurality of first conduits via the at least one second aperture.

2. The manifold of claim 1, wherein each of the plurality of first conduits includes a plurality of first apertures.

3. The manifold of claim 1, further comprising:
    wherein each of the plurality of first conduits includes a plurality of second apertures; and
    wherein the plurality of second apertures are uniformly spaced from one another.

4. The manifold of claim 1, further comprising an end cap adapted to be coupled to a distal end of the manifold to form a distribution space.

5. The manifold of claim 1, wherein each of the plurality of first conduits has a circular cross-sectional shape.

6. The manifold of claim 1, wherein a cross-sectional shape of each of the plurality of first conduits is one of an ellipse, a diamond, a triangle, a square, or a polygon.

* * * * *